(12) United States Patent
Piper et al.

(10) Patent No.: US 7,383,134 B2
(45) Date of Patent: Jun. 3, 2008

(54) METHOD AND/OR SYSTEM FOR ANALYZING BIOLOGICAL SAMPLES USING A COMPUTER SYSTEM

(76) Inventors: James R. Piper, 1 Ards Pl, High Street, Aberlady (GB); Ian Poole, 13 Hamilton Terrace, Edinburgh (GB); Thomas Richard Lörch, In der Holzrott 6, Reilingen (DE)

( * ) Notice: Subject to any disclaimer, the term of this patent is extended or adjusted under 35 U.S.C. 154(b) by 803 days.

(21) Appl. No.: 10/342,804

(22) Filed: Jan. 14, 2003

(65) Prior Publication Data

US 2003/0170703 A1  Sep. 11, 2003

Related U.S. Application Data

(60) Provisional application No. 60/349,318, filed on Jan. 15, 2002.

(51) Int. Cl.
*G06F 19/00* (2006.01)
*G06F 17/00* (2006.01)
*G11C 17/00* (2006.01)

(52) U.S. Cl. ............................ 702/19; 703/11; 382/128; 382/129; 382/133; 435/4; 435/6

(58) Field of Classification Search ..................... None
See application file for complete search history.

(56) References Cited

U.S. PATENT DOCUMENTS

| | | |
|---|---|---|
| 4,833,332 A | 5/1989 | Robertson, Jr. et al. |
| 5,707,797 A | 1/1998 | Windle |
| 5,780,857 A | 7/1998 | Harju et al. |
| 5,830,645 A | 11/1998 | Pinkel et al. |
| 5,936,731 A | 8/1999 | Cabib et al. |
| 6,040,139 A | 3/2000 | Bova |
| 6,146,593 A | 11/2000 | Pinkel et al. |
| 6,210,878 B1 | 4/2001 | Pinkel et al. |
| 6,225,636 B1 | 5/2001 | Ginestet |
| 6,226,392 B1 | 5/2001 | Bacus et al. |
| 6,242,184 B1 | 6/2001 | Singer et al. |
| 6,413,780 B1 | 7/2002 | Bach et al. |
| 6,651,008 B1 * | 11/2003 | Vaisberg et al. .............. 702/21 |
| 6,704,454 B1 * | 3/2004 | Spence et al. .............. 382/240 |

OTHER PUBLICATIONS

Lorch, T. "Automatic Her2 FISH scanning using tile sampling." Metasystems Application Note No. 5. 2002, pp. 1-2.

Wang, S. et al. Aneusomy 17 in Breast Cancer: Its Role in HER-2/neu Protein Expression and Implication for Clinical Assessment of HER-2/neu Status. Modern Pathology. Feb. 2002, vol. 15, No. 2, pp. 137-145.

J.A. Bilmes, A gentle tutorial of the EM Algorithm and its application to parameter estimation for Gaussian mixture and hidden Markov models, ICSI-TR-97-021, International Computer Science Institute, Berkeley, CA 94704, Apr. 1998 pp. 1-13.

* cited by examiner

*Primary Examiner*—John Brusca
*Assistant Examiner*—Jason Sims

(57) ABSTRACT

A method and/or system for making determinations regarding samples from biologic sources. A computer implemented method and/or system can be used to automate parts of the analysis.

52 Claims, 7 Drawing Sheets
(3 of 7 Drawing Sheet(s) Filed in Color)

| "GRID" MODE OPTIONS |
|---|

| | |
|---|---|
| 101 | Use Grid Sampling (click here to select) |

If cell selection is not possible or desired, "Grid Sampling" can be enabled here so that sub-images on a regular grid will be analyzed. The size of these samples is the same as the gallery image size selected.

| | |
|---|---|
| 102a | N Samples per Field X (click here to change) |

With Grid Sampling active, specifies the number of grid samples per capture field in the X axis.

| | |
|---|---|
| 102b | N Samples per Field Y (click here to change) |

With Grid Sampling active, specifies the number of grid samples per capture field in the Y axis.

| | |
|---|---|
| 103a | Overlap of Image Fields X (click here to change) |

| | |
|---|---|
| 103b | Overlap of Image Fields Y (click here to change) |

To avoid losing positive cells lying on the border of a field, an overlap between neighboring image fields can be used and specified above for the X axis (in μm) and/or the Y axis and should be greater than or equal to the diameter of a cell. With enough cells, one can use an overlap of 0, which will increase the overall speed. Overlap can also be specified here for the X and Y axis separately.

*FIG. 5*

METHOD AND/OR SYSTEM FOR ANALYZING BIOLOGICAL SAMPLES USING A COMPUTER SYSTEM

CROSS REFERENCE TO RELATED APPLICATIONS

This application claims priority from U.S. provisional patent application No. 60/349,318, filed Jan. 15, 2002, which is incorporated herein by reference.

COPYRIGHT NOTICE

Pursuant to 37 C.F.R. 1.71(e), applicants note that a portion of this disclosure contains material that is subject to and for which is claimed copyright protection, such as, but not limited to, source code listings, screen shots, user interfaces, or user instructions, or any other aspects of this submission for which copyright protection is or may be available in any jurisdiction. The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

The present invention relates to the field of analyzing tissue and/or cell samples. More specifically, the invention relates to a computer implemented or computer assisted method for making certain determinations regarding samples from biologic sources.

BACKGROUND OF THE INVENTION

Gene Copy Number and Gene Expression

Normal human cells contain 46 chromosomes in 22 autosome pairs and 2 sex chromosomes. Generally, normal cells contain two copies of every gene (except sex-linked genes in males). In both constitutional genetic diseases such as Down syndrome and acquired genetic diseases such as cancer, this normal pattern can be disrupted. The gene copy number of some genes may be more than two (a "gain" or amplification of gene copy number) or fewer than two. Chromosome number can also be disrupted, with cancer cells in particular showing patterns of gain or loss of whole chromosomes or chromosome arms. The number of copies of a chromosome is also referred to as its "ploidy".

In cancer, it frequently happens that the copy number of some genes is greater (often much greater) than the copy number of their corresponding chromosomes. This phenomenon is at times referred to as gene amplification or amplification. Various patterns of gene amplification are characteristic of certain cancers and some other conditions and can inform diagnosis, prognosis and/or treatment regimes.

Genes influence the biology of a cell via gene "expression," which refers to the production of the messenger RNA and thence the protein encoded by the gene. Gene copy number is a static property of a cell established when the cell is created; gene expression is a dynamic property of the cell that may be influenced both by the cell's genome and by external environmental influences such as temperature or therapeutic drugs.

In genetic diseases, gene expression and/or protein expression is also frequently disrupted. In cases where a gene is gained or amplified there is often (though not invariably) a corresponding increase in the expression of that gene, referred to as overexpression. Thus, amplification and overexpression are often, but not always, correlated.

Thus, it is frequently desired to measure and/or determine and/or estimate gene copy number in cells and/or tissues. At present, gene copy number can be measured using a variety of techniques, including quantitative PCR, in situ measuring, and other techniques that attempt to count or estimate the number of specific genetic sequences.

In situ Hybridization and FISH

The technique of fluorescent in situ hybridization (FISH) is used in a variety of clinical and research settings. Generally, the technique is used to locate chromosomal location(s) of specific DNA (or RNA) sequences. A complementary probe is labeled with a fluorescent dye and is then added to a chromosomal or cell preparation from the species of interest. After a sufficient time for annealing to occur, the chromosomes are viewed using a fluorescent microscope. The probe will hybridize to the chromosome carrying the sequence of interest. If the sequence has been characterized cytogenetically, the marker can be assigned to the appropriate chromosome.

FISH analysis has been useful for studying human diseases. For example, if a patient suffering a disease is determined via FISH analysis to have a deletion at a specific chromosomal locus, then the gene responsible for the disease is likely to reside on the missing segment. FISH analysis of tumor tissues can in some cases reveal chromosomal additions, deletions and/or substitutions that may be characteristic of some cancers or other conditions of interest.

More recently, many various strategies and techniques have been proposed for improving and/or automating research and/or diagnostic tests using FISH analysis. Many references describe a range of techniques and methods utilizing FISH. Among these are the following issued U.S. Pat. Nos. 4,833,332; 5,780,857; 5,830,645; 5,936,731; 6,146,593; 6,210,878; 6,225,636; and 6,242,184.

The discussion of any work, publications, sales, or activity anywhere in this submission, including in any documents submitted with this application, shall not be taken as an admission by the inventors that any such work constitutes prior art. The discussion of any activity, work, or publication herein is not an admission that such activity, work, or publication was known in any particular jurisdiction.

SUMMARY

The present invention involves techniques, methods, and/or systems for analyzing biologic samples such as tissue and/or cell samples. In specific embodiments, the invention is directed to research and/or clinical applications where it is desired to analyze samples containing multiple cells. The invention is further directed to applications where it is desired to analyze tissue samples of solid tissues, possibly containing multiple overlapping cells, by analyzing an image of the sample. This image can be a two-dimensional image and/or projection of the sample or, in other embodiments, a three-dimensional image. According to embodiments of the invention, an image is digitally captured by and/or transmitted to an information processing system. Specific embodiments are directed to techniques, methods and/or systems that allow analysis of a tissue sample image containing multiple cells, particularly by an information processing system, even when it is difficult to distinguish well-separated cells in the image.

In certain embodiments, the invention involves methods and/or systems for the estimation of gene copy number and/or detection of gene amplification in tissue samples. In particular embodiments, estimates of gene copy number can be used to accomplish or assist in diagnoses of a variety of diseases or other conditions.

In certain embodiments, gene copy numbers are measured and/or estimated using one or more imaging techniques, such as in-situ hybridization (ISH) techniques. (FISH), for example, generally produces visible colored "spots" at areas where sequences complementary to probes are detected. Other imaging techniques use various non-fluorescent optical (e.g., haematoxylin-eosin (H&E) viewed in brightfield) or radiographic or electrographic signals to image a sample. Thus, the invention is particularly of interest in various computer systems and/or methods used to capture and/or analyze images of biologic interest.

Example Application: Detecting HER-2/neu Amplification

While the invention broadly involves methods relating to measuring and/or estimating biologic characteristics of samples, the invention may be further understood by considering as an example the problem of determining whether a particular breast cancer is likely to respond to treatments targeting HER-2/neu gene overexpression. It is currently believed that one method of determining if a breast cancer will respond to treatments targeting HER-2/neu, such as Herceptin™, is by determining and/or estimating HER-2/neu copy numbers in cells that are identified as invasive cancer cells.

It is generally believed in the field that breast cancer lesions divide into two main types, namely ductal carcinoma in situ (DCIS) and invasive cancer. Tumors that are exclusively DCIS are generally treated by surgery with a high success rate, and Her2 status of those cells is generally not of interest. If the tumor contains both DCIS and invasive regions, the Her2 amplification status in DCIS may not always correspond to the status of the invasive lesion. Therefore, to be informative, Her2 amplification generally is most of interest in invasive cancer cells.

One way to determine amplified HER-2/neu gene copy number in a cell or sample of cells is to compare a number of detected HER-2/neu genes to a number of detected copies of HER-2/neu chromosome 17. In each normal and unamplified cancer cell, there should be detected two HER-2/neu genes and two copies of chromosome 17. CEP17 is a FISH probe that labels the chromosome 17 centromere and is used to count chromosome 17 number. LSI-Her2 (or Her2 for short) is a FISH probe commercially available from Vysis, Inc., Downers Grove, Ill., that labels the HER-2/neu gene. Thus, the ratio of Her2 to CEP17 counts detected in a cell or sample can indicate whether the HER-2/neu gene is amplified. More generally, this ratio can be understood as the ratio of test values or counts ($t_i$) to control values or counts ($c_i$) over a designated cell, region, tile, or sample. At times below, this ratio is referred to as the Tumor Ratio (R), to indicate the ratio ($t_i/c_i$) in cells or other sample regions that have been identified as being of interest, e.g., tumor cells.

Typically, when analyzing an image of a tissue sample, determining such ratios requires a number of different tasks, each of which can present difficulties. For example, these can include (1) determining areas of an image that contain abnormalities indicating invasive cancer cells, which is often done by inspection of tissue architecture using H&E staining of a parallel tissue section; (2) distinguishing individual cells; (3) of the distinguished cells, determining by size and/or morphology which are invasive cancer; and (4) for each invasive cancer cell individually and/or for them all, determining a t/c ratio of interest, such as Her2/CEP17.

While this specific problem of determining HER-2/neu amplification will be used as an example of the invention, the invention is applicable to other situations that call for cell and/or tissue analysis. Several research and clinical investigations in cancer involve counting the number of FISH spots in tumor cells present in thin sections from tissue biopsies and in the future greater use may be made of 3-dimensional imaging as well. Other investigations make use of the intensity of immunochemical staining of cells in tumor material. Yet other analyses, for example in hematology, use the number of FISH spots per cell in cellular monolayer preparations. These and other similar situations often will require similar steps to those described above and are also applications of embodiments of the invention. In particular, the present invention can be used in characterizing or diagnosing a variety of different diseases.

With various imaging techniques, such as FISH, it has been proposed to base ratio estimations and/or counts on well-separated cells only, with either automated or operator-directed discrimination of cells of interest. This method is referred to herein as the cells method. In specific embodiments, the present invention involves analysis techniques that can improve sample analysis using the cells method.

However, because isolated cells may be rare in regions of interest, and because both segmentation of overlapping cell nuclei and discrimination of tumor from normal cells are likely to be difficult, the invention in specific embodiments, further utilizes alternative methods, generally referred to herein as tiles-based method. Tiles-based analysis according to some embodiments of the invention can involve placement of tiles in some regular arrangement; this is referred to herein as grid tiling. Tiles-based analysis according to other embodiments involves placement of tiles according to a targeting rule set or algorithm; this is referred to herein as targeted tiling.

Thus, in specific embodiments, the invention provides a method of analyzing biological samples using an information system to place tile outlines over an image of a sample and/or to perform analysis of data determined from a sample. In some embodiments, the invention analyzes the image by scoring characteristics within one or more outlines and prepares output from scored characteristics. A tissue sample can be a variety of samples, such as, a dense cellular monolayer prepared from disaggregated cells, a smear preparation, etc. An image can be derived from a sample using a variety of techniques, such as extended focus or a simple two-dimensional image of visible light or other detectable signals. Tiles can be placed according to a variety of methods in specific embodiments of the invention, including, for example, searching for a desired signal strength of a detectable signal over the sample.

A detected signal used according to specific embodiments for tile placing can include such signals as, for example, total fluorescence intensity in a tile of a nuclear DNA stain and searching can, for example, search for a tile outline region that produces a highest value of a signal or a value above a cutoff. A ratio of two signals can also be used.

Analyzing tiles can include such things as counting the occurrences of one or more signal values in a placed tile outline and possibly using a ratio of signals.

Outputs of a system according to specific embodiments of the present invention can include such values of diagnostic interest as: an estimation of gene copy number; detection of gene amplification.

A variety of tile outline shapes can be used in systems and/or methods of the invention, with typical tile shapes being either generally circular or polygonal and tiles typically selecting to have an area equal to or slightly larger than a largest cross-sectional area of a largest expected cell in a sample.

Various methods for analyzing tiles (or cells or other sample subsets) can be employed in specific embodiments, such as in each subarea, computing histograms of ratios from detectable signals and estimating a ratio value for, for example, tumor cells in a sample from normal-corrected histograms. In specific embodiments, other statistical methods and refinements can be used in estimating and normalization.

The invention can also be embodied as a computer system and/or program able to analyze captured image data to estimate observable features of said data and this system can optionally be integrated with other components for capturing and/or preparing and/or displaying sample data.

Various embodiments of the present invention provide methods and/or systems for diagnostic analysis that can be implemented on a general purpose or special purpose information handling system using a suitable programming language such as Java, C++, Cobol, C, Pascal, Fortran, PL1, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

When used herein, "the invention" should be understood to indicate one or more specific embodiments of the invention. Many variations according to the invention will be understood from the teachings herein to those of skill in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 illustrates example user interfaces for grid tiling options according to the present invention.

DESCRIPTION OF SPECIFIC EMBODIMENTS

1. Preparation of Tissue Sample and Capturing an Image for Analysis

In a specific example embodiment, the present invention can be used to automate and/or assist in analysis of samples of tissue and/or cells. FISH is one sample labeling technique that can be employed in accordance with the invention, but it will be understood from teachings herein that analogous methods and/or systems can be utilized, e.g. those using radioactive and/or electroactive probes or using sample characteristics that are discernable without use of probes.

In a more specific example, DAPI (4,6 diamidino-2-phenylindole) can be used to generate a signal indicating nuclear DNA. DAPI fluoresces (generally blue) when exposed to ultraviolet light (UV). Some analyses of interest can use a DAPI signal only. In other analysis, one or more additional FISH probes are used, with DAPI used as the counterstain. FISH probes can be labeled with dyes such as SpectrumOrange or SpectrumGreen so that they can be distinguished against the DAPI background by their different colors.

Figure 1:
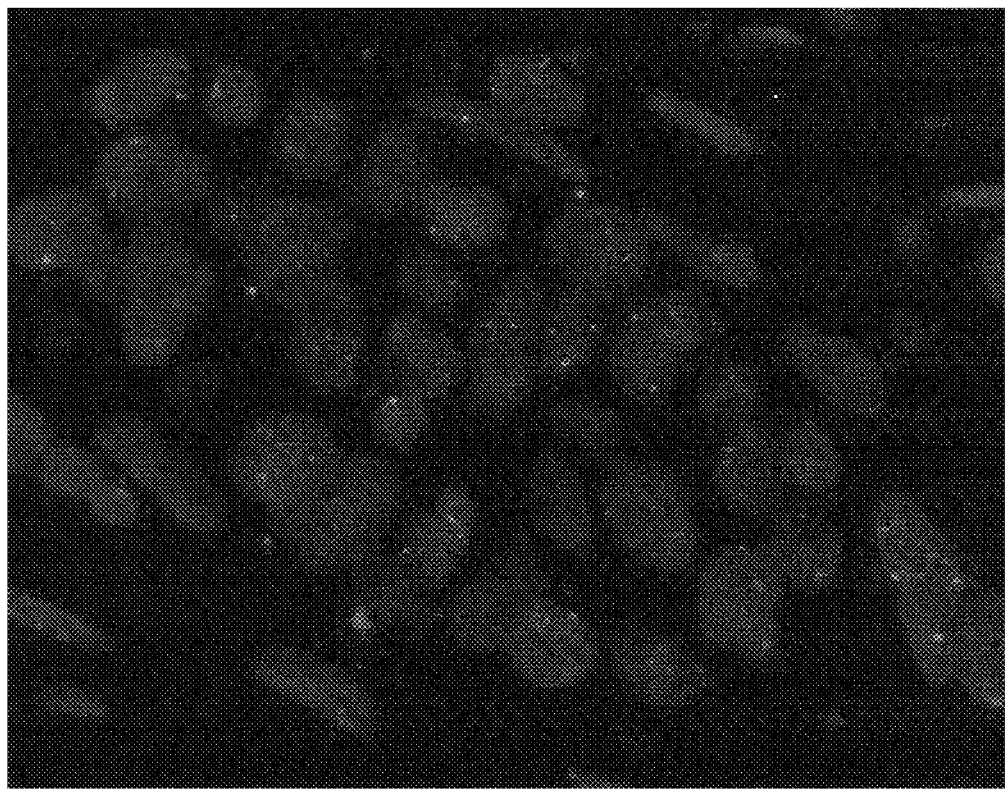
FIG. 1 illustrates an example image of a sample labeled with different probes to which techniques or systems according to the invention can be applied.

FIG. 1 illustrates an example image of a sample labeled with different probes to which techniques or systems according to the invention can be applied. (In black and white reproductions of this figure, areas of the image that would be seen as light blue fluorescence are shown as light gray, areas that would show as green fluorescence and red fluorescence are shown as darker gray spots in the light gray areas. Note that the image shown in FIG. 1 is a two-dimensional projection of three-dimensional cells. Such an image will typically include some projections of cells that have been cut during the sample preparation process and include some images of overlapping cells. In this projection, blue fluorescence indicates DAPI labeled nuclear DNA with the outlines roughly indicating projections of cell nuclei. Thus, a round or elliptical blob is usually the projection of the nucleus of a single cell, while a larger blob with a more complex shape will usually be the projection of the nuclei of several overlapping cells. The present invention can be adapted to situations where the intensity and/or shape and/or size and/or other characteristics of these areas are used to make a diagnosis or differentiation of interest.

A captured image area of a sample, such as that shown in FIG. 1, is sometimes referred to as a field of view or FOV. This term generally indicates an image of a sample or part of a sample that is captured as one image by a capture device (such as a CCD camera). In other context, FOV can also apply to what is visible at one time through eyepieces of a viewer or microscope, though this is more clearly referred to as a "visual field."

Another term of interest is for specific embodiments is selected area. As will be generally understood in the art, selected area refers to a region of a sample that has been determined to contain invasive tumor material. Usually, this determination is made by a skilled technician or pathologist, though other mechanisms, including automatic screening mechanisms are possible and well-known in the art. In practice, a single FOV can be a selected area.

In specific embodiments, the invention can be used with extended focus image capture, as is known generally in the art. In such a procedure, images at different focal (Z) positions are captured by a capture device (such as a CCD camera) and are stored. The number and the distance of these focal planes are generally settable in different specific embodiments and are adapted to the thickness of the specimen and the depth of focus of the microscope objective. An algorithm is then used to combine the different images into a single image. For example, when the entire stack of images has been captured, a local focus criterion is used to select independently for each XY position the focal plane (Z position) from which the pixel's intensity is taken. Suitable focus criteria include but are not limited to such things as absolute intensity, local contrast, local sum of absolute gradients, etc. In further embodiments, a Z position of the focal plane from which a pixel value was taken is stored in a separate image, enabling the computation of three-dimensional distances.

2. Determining Specific Areas of an FOV or Captured Image for Analysis

With an image like that shown in FIG. 1, one task is to determine how to analyze the signals in the image. In general, it is desired to analyze signals in relation to estimated cells. For example, a researcher might want to know the range of intensity of DAPI signals of different cells. In order to do this, generally some association must be made between areas of the image and cells.

Separated Cells Approach

In cells-based approaches, image analysis generally includes an attempt to determine those areas of the image that correspond to individual cells. Generally, only well-separated cell images are used. However, isolated cells may be rare in sample regions of interest and such a method, particularly when automated, may produce inaccurate results and/or miss important cell regions.

Grid Tile Placement According to the Invention

The invention in certain embodiments processes an image such as FIG. 1 using a grid-tiling approach. In such an approach, a regular or semi-regular grid is laid down over part of the image of interest. In a simple method, a grid is simply superimposed over the sample image, with, for example, the beginning of the grid starting at the beginning of the image. Tiles are then analyzed as discussed further below. A variety of different optimizations in such a grid tiling approach can be used, such as beginning a grid only where a certain density of DAPI signal is reached, adjusting or optimizing grid tile sizes, adjusting or optimizing the amount of grid tile overlap, adjusting grid tile shape, etc.

An embodiment related to this method has been incorporated in a software package called Metafer™, which is believed to have been available for less than one year before the priority date of this application. Further details of this embodiment are discussed in the above referenced patent application(s) and appendices. An example of a portion of a user interface discussing some options in a grid-tiling software system according to specific embodiments of the invention is shown in FIG. 5.

Targeted Tiling According to the Invention

Figure 2:
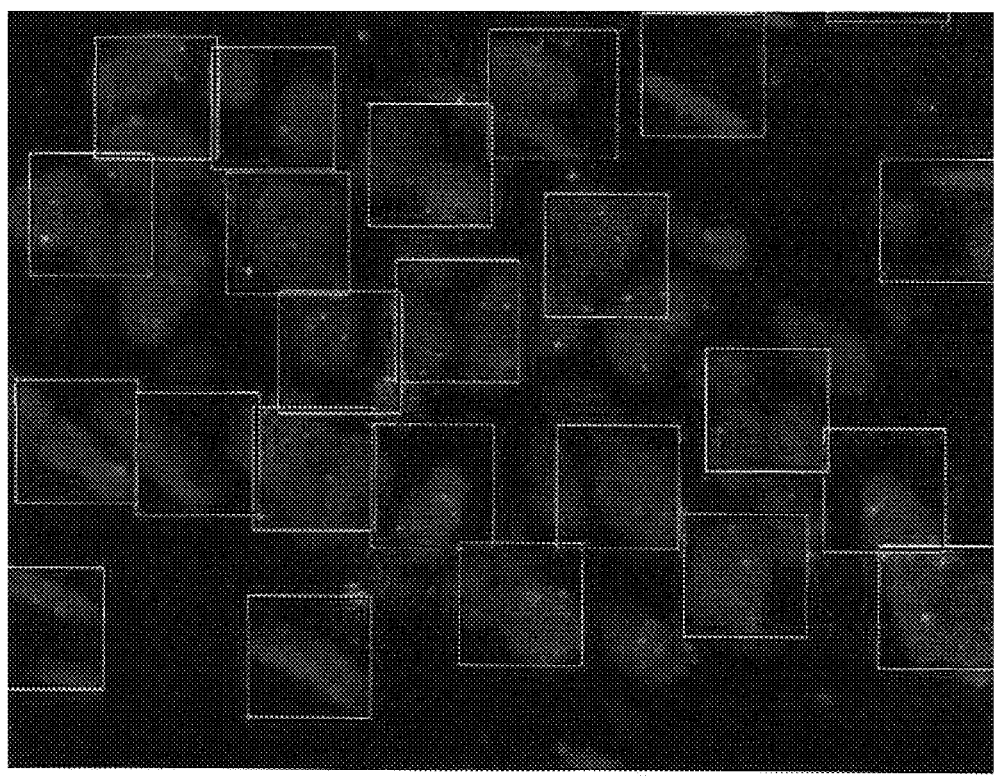
FIG. 2 illustrates an example image of a sample with targeted tiles placed according to the invention.

Further embodiments of the invention analyze an image such as FIG. 1 using a targeted-tiling approach. In this approach, a computer-implemented method analyzes the image and determines a plurality of tiles to place over the image according to one or more logical rules. As discussed below, tiles can be of various shapes (such as polygonal or elliptical) and can vary in size. However, certain embodiments use square tiles of the same size. As will be seen below, this embodiment can be simpler to describe and can make some calculations more straightforward. In various embodiments, tiles can be non-overlapping or may overlap to various degrees. FIG. 2 illustrates an example image of a sample with targeted tiles placed according to the invention. In this example, square tiles of the same size are used, and tiles are non-overlapping.

Thus, in certain embodiments, tile positions are selected by an information processing system iteratively in each FOV or selected area. In particular embodiments, each successive tile is placed within the remaining untiled areas of the FOV to include maximum DAPI intensity. Placement of tiles is stopped according to one or more end conditions, such as: (i) when the maximum DAPI intensity in the remaining non-tiled area is less than a lower threshold, and/or (ii) when there are no areas where a non-overlapping tile can be placed and/or (iii) when the total DAPI intensity of the last placed tile falls below a threshold. While the example described uses a signal such as DAPI-intensity to target tiles, other signals (such as radioactive labels) or other image characteristics (such as image or staining density, etc.) may be used.

3. Comparing Sample Analysis Methods

Cells approach: If all cells are identified correctly, this method samples tumor cells only. However, this approach relies generally on the premise that normal cells are visually distinguishable from the tumor cells, but such discrimination generally requires a skilled technician or pathologist and is subject to errors or varying interpretations. In an automated system, cells of interest are less likely to be identified correctly. As the accuracy of automated discrimination gets worse, this method degenerates towards the "area total" method.

Area total method: In this method the ratio is based on value measures or spot counts (e.g., Her2 and CEP17) summed over a larger area, with no attempt made to discriminate areas of interest. This can effectively dilute a signal of interest (e.g., HER-2 amplification signal), because in many samples a significant portion of a region may be normal. For example, some pathologist reports that at times some breast tumors can include 90% normal cells in a tumor region. The proportion of a sample that is of interest is sometimes referred to as the Tumor Proportion (P), which in the previous example would be 10%. More typically, Tumor Proportions can range from 30 to 100%

Tiles approach: This method of the invention reduces dilution of the overall ratio by plotting per-tile (or similar sub-area) ratios. However, per-tile ratios can be noisy due to various factors, for example: (a) the method may sample tumor and normal cells in the same tile (sometimes referred to as random dilution of tiles); (b) cell truncations due to tiling, etc. However, according to the invention, using sufficient tiles allows the estimated overall ratio to nevertheless be diagnostic.

4. Example Rules for Targeted Tiling

In certain embodiments, targeted tiles are placed according to one or more rule sets on information processing apparatus, as will be understood in the art. An example rule set for placement of tiles is as follows:

I. Determine a desired tile shape and/or size. In some embodiments, this may be determined by prior experimentation. In other embodiments, this may be automatically determined by an analysis of the image. In other embodiments, this may be determined with assistance or direction of a human operator.

II. Scan the image and place a first tile over the area that provides the maximum total DAPI signal or other detectable characteristic of interest in that tile area.

III. Scan the remaining areas of the image (allowing for overlap in specific embodiments) and place a next tile over the area that provides the maximum total signal of interest in that tile area, optionally while testing for a stop condition.

IV. Repeat III until a stop condition is reached.

Using such a rule set, tiles generally are successively positioned optimally to sample cellular regions in a FOV, but not to sample acellular regions. A number of variations and options are possible within a general rule set, some examples of which are discussed below.

Tile Size

In certain embodiments, tile size is selected to be large enough to completely include an expected cross-section of tumor cell nuclei. This can be referred to as a size=1 tile. Alternatively, a tile may be used that is a somewhat larger than this, to increase the chances of capturing an entire nucleus in a tile. For example, a tile that is 110% of the size needed to completely include an expected cross-section of a cell nuclei of interest can be referred to a size=1.1 tile. Some experimental work has been done with size=2 and size=4 tiles.

Overlapping Tiles

In specific embodiments, tiles are placed so that tiles are strictly non-overlapping. Other embodiments can allow tiles to overlap somewhat, or under certain conditions. For example, according to further embodiments, a DAPI positive filter can be generated, with, for example, ½ to ¼ tile overlapping images used to determine the ratio of test to control signal only within the DAPI positive image. In this embodiment, overlapping is used to reduce the risk of splitting tumor cells. An advantage to not overlapping, however, is independence of the tiles. With overlapping tiles, it is possible to count the same event two (or more) times.

Circular, Elliptical, or Other Shaped Tiles

Tiles need not be square or rectangular. Circular, elliptical, hexagonal or other shaped tiles can be used to achieve fewer contributions from other cells (less mixing) and a higher density of tiles. Such tiles can be set to a size or shape just slightly larger than the average cell nucleus, therefore, more closely approximating an area that would be manually counted and thereby reducing the chance of counting signals in fractions of adjacent cell nuclei.

Other Options

While in some embodiments, tiles are placed solely to maximize a signal (such as DAPI) in the tile area, other embodiments can include more complex placement algorithms, such as algorithms that attempt to center a tile near the center of a signal density or that compare or combine two or more signals.

5. Analysis Using Additional Probes

While some cell characteristics of interest may be measured using a single probe, the signal of which is also used in targeted tile placement, a variety of other analysis will be aided by the addition of one or more additional probes. In some cases, just one probe may be used to identify a signal that according to specific embodiments of the present invention is further associated with placed tiles and/or with a DAPI-like signal. Thus, the targeted tile approach can be used in principle for a single color channel.

In other situations, however, more than one probe is used and the signals can be correlated to indicate characteristics of the cell. For example, some existing kits for Her2 measurements use two color channels (DAPI plus one channel with FISH signals). Targeted tiling according to the invention can be used in this situation to determine areas of analysis of the Her2 signal.

As a further example, in the sample image shown in FIG. 1, two probes in addition to DAPI (resulting in three color channels) are included in the sample preparation, one labeled with a green fluorescent dye and one with an orange fluorescent dye. In various examples, the green signal can indicate a control signal of interest and the orange signal can indicate a test signal of interest. Various cancers and other conditions of interest may be associated with differential spot counts or values of such signals.

As a more specific example, consider Her2 analysis. At present, using FISH, it is generally believed that detection of Her-2/neu amplification can be accurately accomplished by determining ratios of Her2 to CEP17 spot counts averaged across tumor cells in regions of invasive cancer. One method bases the ratio estimation on well-separated cells only, with automated discrimination of tumor and normal cells. The present invention, according to specific embodiments, provides a better means of detecting Her2 amplification. According to further embodiments, the invention can be embodied in a Her2 scanner system for automatically measuring the degree of Her2-amplification in tumor biopsies.

6. Spot Counting

According to the invention, spot counting (e.g., FISH) within a tile can be conducted by methods similar to those known for spot counting of isolated cells. For example, generally only spots within the DAPI mask are counted. For targeted tiles, each placed tile is expected to include an amplified tumor nucleus, an unamplified nucleus, or parts of one or more nuclei of either type, including mixtures of the two types.

It will be understood that spot counts will be randomly reduced by truncation by the tile boundaries in X and Y. This is similar in principle to the reduction of per-cell spot counts by the physical (e.g., slicing) truncation in Z. In specific embodiments, it is possible to detect and/or measure signal amplification from the spot count distribution from a large enough sample of tiles, particularly when the proportion of amplified tumor cells to unamplified cells is sufficiently large. (Generally, in HER-2 amplified invasive cancers, it is expected to be 10% or greater in almost all samples.)

Counting according to specific embodiments of the present invention can be done entirely automatically by an information processing system, without intervention of a human operator. It will also be understood that counting can be performed or supplemented by display to a human operator and human evaluation. In various displays, tiles can be presented in a gallery, sorted either by signal ratio or by spot count, both as determined by an information processing component. Spot counts can be corrected in the gallery of tiles, in ways similar to correction in a gallery of isolated cells (though, in specific embodiments, the number of tiles might make this impractical). In specific embodiments, tiles can be rejected by the user, for example if they contained non-cellular debris. In a particular embodiment, as discussed above, a human operator designates areas to be tiled that contain invasive tumor cells.

Gallery Review

Figure 3:
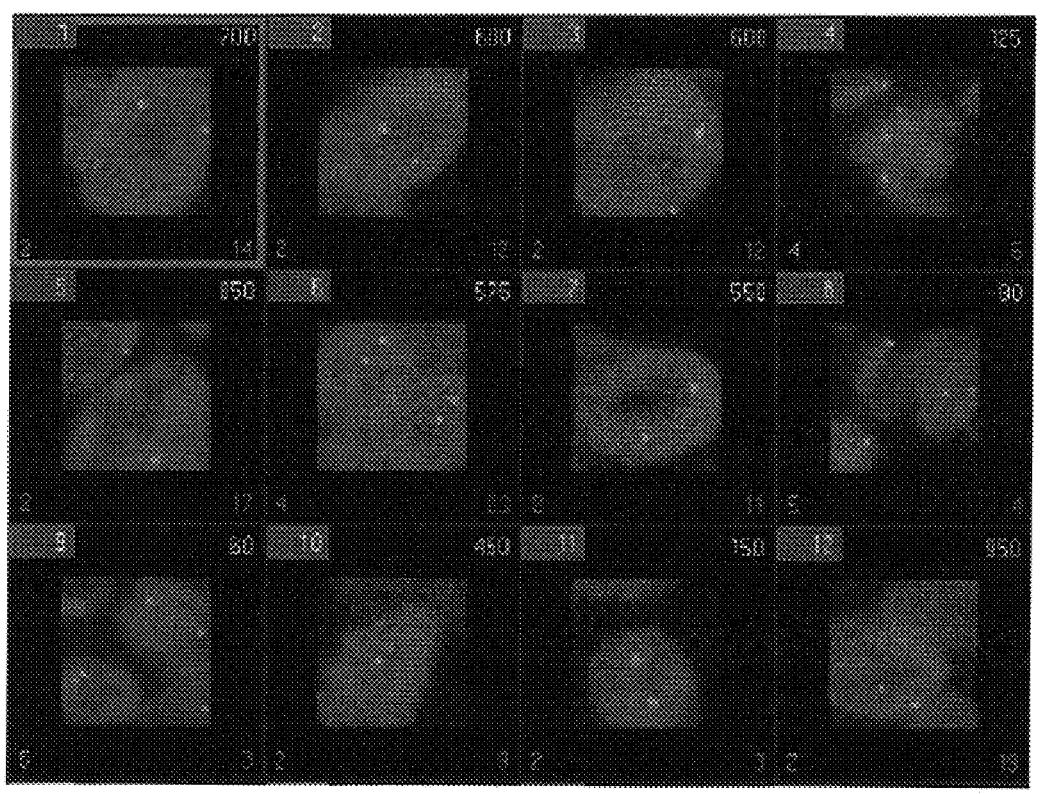
FIG. 3 illustrates an example of a gallery review that can be employed with the invention.

In cell-based computer analyses, it is conventional to display all cells, or just those cells that are selected by some criteria, on a screen in a two-dimensional array of generally equal-sized images. This display is commonly known as a "Gallery." In specific embodiments of the invention, tiles are displayed in the same way, so that the system operator can review the actual per-tile FISH spot counts on which the ratio estimate is based. FIG. 3 shows an example of such a gallery display, again modified to a black and white image.

7. Example Operator Participation Scenario

As discussed above, the invention can be embodied in a system that performs a number of steps automatically and also provides display to a user and interacts with a user to complete scanning. These operations will be described using a specific example of Her2 amplification detection:

1. A user indicates selected regions of invasive cancer by marking or selecting regions as described above from a display of a sample tissue (in specific embodiments, with the requirement that each region have at least N tumor cells.)
2. An information processing component of the invention analyzes each region as described herein, placing tiles to cover most of the nuclear material visible to cover the predefined area around one or more marked spots.
3. A display gallery according to the invention presents one or more tiles, sorted by, for example, ratio or Her2 spot count, etc., for review by the operator if desired.
4. Optionally, a user can confirm (e.g., by clicking on a screen button) that enough tumor cells have been included in the tiles presented in the tile gallery to obtain a reliable estimate of the Her2 to CEP17 ratio from the tiles analysis. If insufficient tumor cells have been included in the scored tiles, then the user has the option of indicating further selected regions of invasive cancer for analysis.
5. A spot count distribution, based on a large number of tiles, is used to estimate Her2 to CEP17 ratio as described in more detail below.

It will be understood from the discussion above that this example assumes that the initial step of identifying a selected region is performed prior to the analysis of Her2 by a tiles method according to the present invention. For breast cancer, this is generally done by human review. In other applications, however, a tiles method can be used to identify the selected regions, either in combination with other analysis or possibly prior to other analysis.

8. Example Data Analysis

The present invention includes various approaches for analyzing samples based on the spot count distribution of the tiles. Some terms and assumptions used below are as follows.

The cell mixture sampled by the tiles consists of a mixture of unamplified cells and amplified tumor cells in initially unknown proportions.

The cell mixture sampled by the tiles contains some tumor cells of interest and for Her2 those are primarily invasive tumor cells. In other words, the selected region was correctly identified.

Unamplified cells may either be normal cells or unamplified tumor cells, and they are assumed to have a test to control ratio of 1.0 (e.g., the same amount of each type of detected values), though methods of handling samples with two different cell populations, neither of which has ratio 1.0, can be used in specific embodiments.

The proportion of amplified material in the analyzed region in this example is the ratio of the total CEP17 control count in amplified cells to the total CEP17 control count in all cells; it thus differs from the proportion of amplified cells in cases where the average CEP17 count is different in amplified and unamplified cells. This can be the case where some or all of the amplified cells exhibit chromosome ploidy. Thus, if 10% of the cells in the sample are amplified tumor cells and all have double chromosome 17, the proportion of amplified cells is 10% □ and □ the proportion of amplified material is (2×0.1)/(0.9+2×0.1)=18.18%. Generally, the proportion of amplified cells cannot be computed in analyses that are not cell-based, for example, tiles analysis.

Computing Ratios from Count Data

In some methods, (e.g., according to the PathVysion™ package insert (PPI)), individual cells that appear to be tumor cells are identified and amplification test spots (e.g., red/orange for Her2) and control spots (e.g., green for CEP17) are counted in each individually identified cell. The amplified ratio (R) is defined to be the ratio of the overall sum of test spots to the overall sum of control spots: $R=(\Sigma t_i)/(\Sigma c_i)$, where i indexes the counted cells, t indicates test spot counts, c indicates control spot counts. In the present invention, this same basic relationship is used, but on a per-tile basis, rather than an individually identified cell basis. Thus, for an alternative formulation, define the ratio of a single cell (or tile) to be $R_i=t_i/c_i$, with $R_i$ set to 1 if $c_i=0$. Then R can be expresed as:

$$R=\Sigma c_i R_i / \Sigma c_i \qquad \text{(Eqn. 1)}.$$

In other words, the ratio R can be expressed as the "the sum of the per-cell ratios multiplied by the per-cell CEP17 counts, divided by the total CEP17 count." Variants on this alternative formulation appear below.

Example Automated Method: Analysis by Subtracting Normalized Reference Histogram One method of the invention is described herein as subtracting a normalized reference histogram. This method starts by collecting per-tile count data and then converting it to a tiles ratio histogram. The ratio of a tile (also $R_i=t_i/c_i$, where $t_i$ and $c_i$ may be values or spots only measured in nuclear areas) will be a rational number or fraction. Such fractions can take a variety of values due to the possibility of aneuploid tumor cells and significant amplification of the target gene in tumor cells. To convert the fractions to a form suitable for a histogram, the ratios are allocated to generally equal-width "buckets." One example is buckets of width 0.5, centered on 0.0, 0.5, 1.0, 1.5, etc., i.e. the bucket boundaries lie at 0.0, 0.25, 0.75, 1.25, 1.75, etc.

Figure 4A:
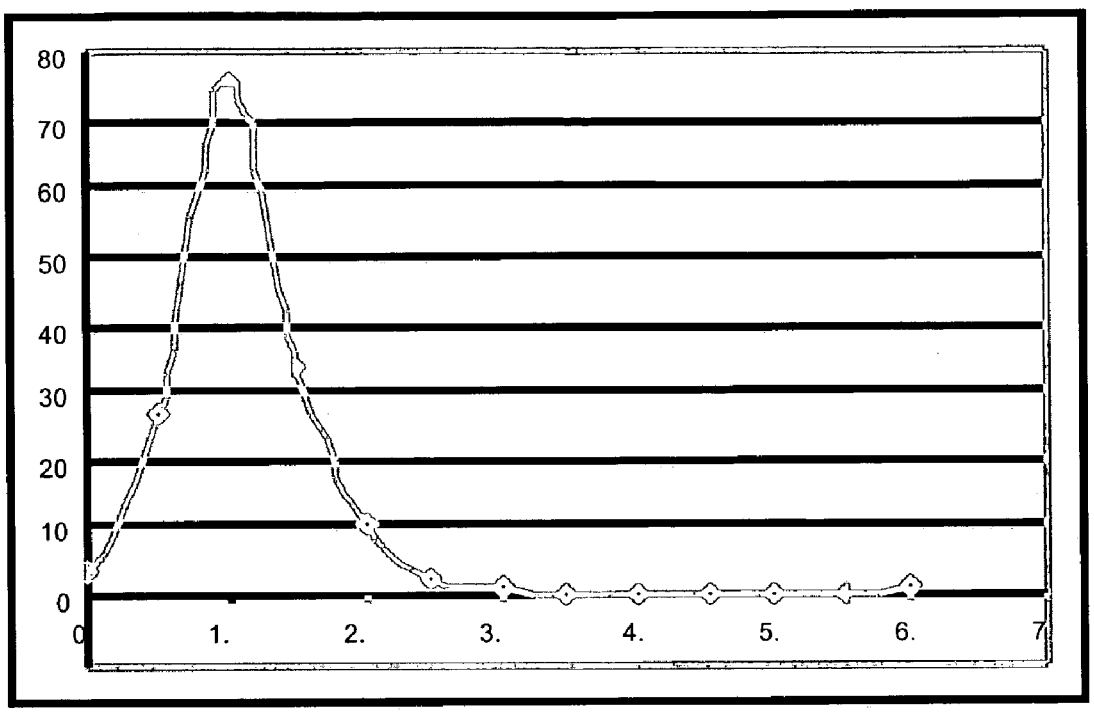
FIGS. 4A-C are example histogram graph diagrams illustrating an analysis method according to the present invention.
Figure 4B:
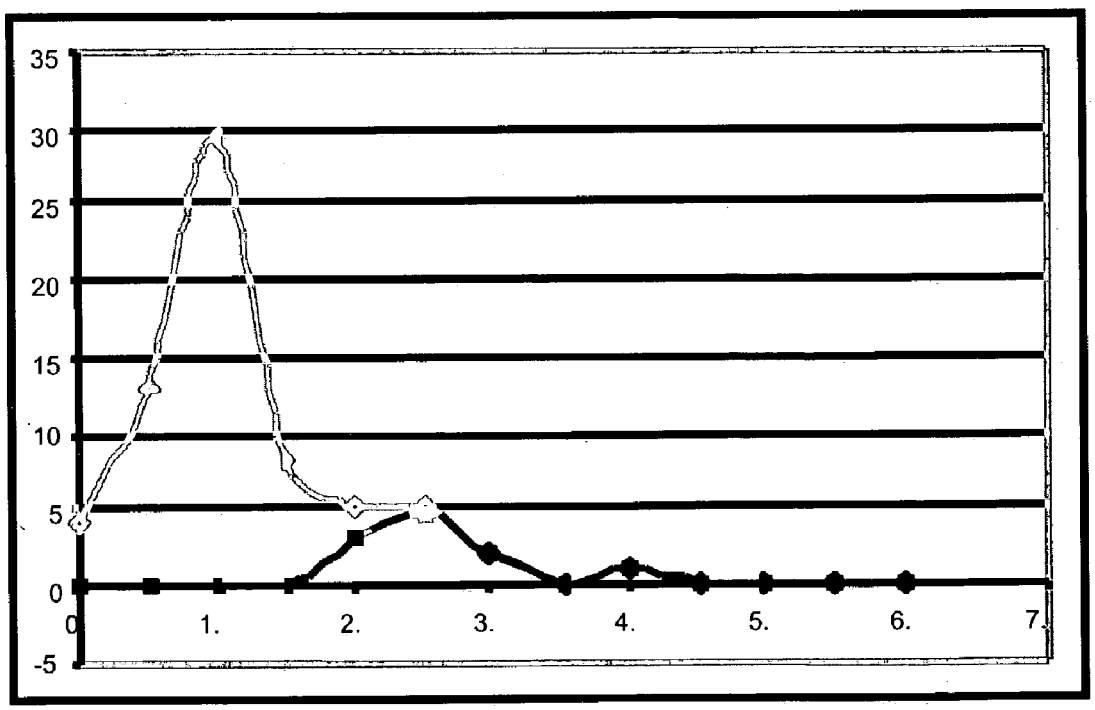
Figure 4C:
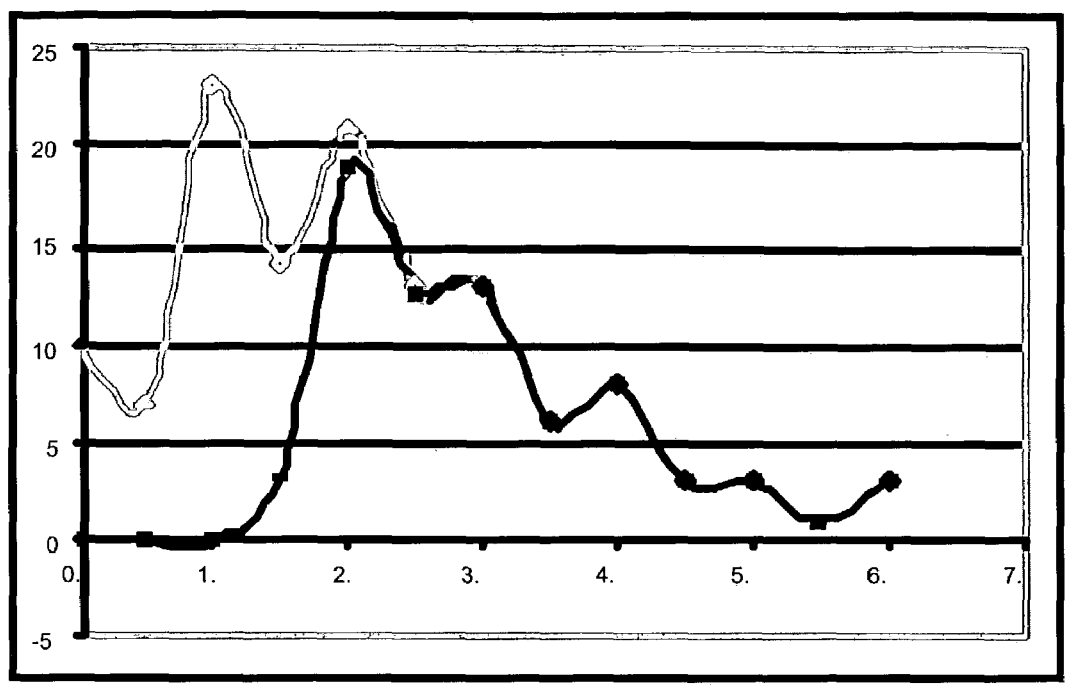

FIGS. 4A-C are example histogram graph diagrams illustrating an analysis method according to the present invention. Both simulation and experiment show that the tiles ratio histogram from a normal sample (e.g. all unamplified cells) will have a shape approximately as shown in FIG. 4A, with a substantial peak at 1.0 falling off quickly on either side. The values to the left and the right of the peak are due to tiles that do not fully image a single cell due to truncation effects, or include parts from more than one cell. The better the targeting of tiles, the more nearly each tile includes exactly one cell, and the more quickly the peak at 1.0 falls off on each side for unamplified samples.

Tiles ratio histogram from a sample that includes a mixture of unamplified cells (e.g., with $t_i/c_i$ ratio 1.0) and amplified cells (e.g., with $t_i/c_i$ ratios higher than 1.0) will generally have a shape with a notable shoulder or a second peak to the right of the 1.0 peak. Two examples of such a histogram, based on real data, are shown by the darker curve in FIG. 4B and FIG. 4C.

One method for extracting the tumor-related tiles according to the invention is to fit a normalized reference histogram shaped like FIG. 4A to the normal peak centered on ratio=1.0 in a mixed tumor histogram, e.g. FIG. 4B and FIG. 4C. It is understood in the art that fitting is a process whereby a reference histogram is matched as closely as possible to a histogram from a sample being analyzed. In certain embodiments of the invention, this is done by proportionately adjusting the counts of the reference histogram buckets so that the normalized reference histogram matches the sample histogram in the unamplified region (say, ratios from zero to 2) as closely as possible. Choice of the optimum proportion may be performed e.g. by minimizing the sum of square differences between corresponding bucket counts. Subtraction of one histogram from another generally results in a third histogram where the count of every bucket is the difference between the corresponding counts of the first and second histogram. According to specific embodiments of the present invention, if this difference for any single bucket is negative, it is set to zero. After histogram fitting and subtraction according the invention, "corrected" histograms are as shown by the gray curve in FIG. 4B and FIG. 4C.

Estimating Tumor Ratio from Tiles Histogram

Note that the histogram figures shown in FIG. 4B and FIG. 4C are counts taken from tiles over a mixture of cells, including tumor and non-tumor cells. According to specific embodiments of the present invention, the invention estimates an overall amplified ratio R directly from the tiles ratio data, without specifically differentiating normal cells from tumor cells.

As an example of such a method, for each histogram bucket indexed by b, let $q_b$ be the proportion of the count remaining after subtracting the normalized reference. Generally, this $q_b$ will be a percentage value. For example, in FIG. 4B above, and using an obvious shorthand notation, $q_{b<1.5}=0\%$, $q_{b=1.5}=0\%$, $q_{b=2.0}=\frac{3}{5}=60\%$, $q_{b=2.5}=\frac{5}{5}=100\%$, and $q_{b>2.5}=100\%$.

Note that it is not necessary for the fitted histogram to have integer count (y-axis) values, but if not, then the corrected histogram will have non-integer y-axis values. This situation can arise during fitting, as the fitting will match a reference histogram to the observed histogram. If the reference histogram values are $S_b$ and the observed histogram values are $H_b$ with b the bucket index, then fitting amounts to minimizing the sum of absolute differences $\Sigma_b(|H_b-wS_b|)$ where w is a constant weight and b indexes the "normal range" (0<b<2). There is no reason for w to be an integer, and so the corrected histogram values $H'_b=(H_b-wS_b)$ may no longer be integer "counts". (Thus, strictly H' it is no longer a histogram, though that term provides an appropriate shorthand.) Note that $q_b=H'_b/H_b$, with negative values replaced by zero.

Next, ratio R can be estimated by applying equation 1 to the corrected histogram, as follows:

$$R=\Sigma_b(q_b c_b R_b)/\Sigma_b(q_b c_b) \qquad \text{(Eqn. 2)}.$$

where $c_b$ is the total CEP17 count of the tiles allocated to bucket b, and $R_b$ is the central ratio of the bucket as defined above.

Verify Tumor Ratios

According to the invention, by analogy with the cell-based definition above, the "proportion of amplified material" can be defined to be:

$$P=\Sigma_b(q_b c_b)/\Sigma_b c_b \qquad \text{(Eqn. 3)},$$

with the computation here being based on the proportions of each histogram bucket that have been identified as being derived from amplified material.

In specific embodiments, it is desirable not to report the ratio R unless P exceeds a minimum threshold, such as, for example, 0.1. This is because if P is very small, experience indicates that the corrected histogram may be dominated by numerical artifacts. This case generally can be recognized by two properties. First, the "overall ratio" of the set of tiles $R_O$ (the total Her2 spot count in all tiles divided by the total CEP17 spot count in all tiles) will be very close to 1.0. Second, since all tiles in this case will have normal ratios except for the effects of cell truncation, the corrected histogram will be a very small proportion of the original histogram, i.e., the estimate of P will be very small. According to specific embodiments, therefore, the histogram fitting method for estimating R is made conditional on (i) an overall ratio $R_O$ significantly different from 1.0, and (ii) an estimated value of P greater than some minimal cutoff. In general, in certain embodiments, these thresholds are established by a calibration experiment.

Numerical Results Reporting

In various embodiments, histogram analysis can provide output in the form of one or more numerical results. Such results can be reported in a spreadsheet or any other desired or convenient form. Examples of numerical results output include: (A) The overall ratio ($R_O$) across all tiles (sum of test values divided by sum of control values). This output generally ignores the problem of a cell mixture of normal and tumor cells, or a mixture of unamplified and amplified cells. (B) The mean ratio (R) of the corrected histogram, intended also to represent the mean ratio of amplified tumor cells. Because this histogram is a construct (i.e., there is no way to identify the tiles removed in the background correction), this ratio is approximated by sum (bucket_ratio*bucket_frequency)/sum(bucket_frequency). However, this method is not very satisfactory because it is equivalent to assuming that all tiles have the same CEP17 count. In practice, tumor regions often show higher tile counts for CEP17, so this method is likely to underestimate the ratio. (C) The proportion of tiles (P) estimated to be composed of amplified cells.

Further Refinements

While the above method works in many situations, further research has indicated areas for improvements. For example, issues to address include what to use as the normalized reference histogram and how to fit it. Analysis has indicated that the best shape of a normalized reference histogram, in certain embodiments, can vary from sample to sample (e.g., it can depend on the typical number of spots in a tile). Using an incorrect reference can introduce significant artifacts. A further issue arises from tiles with a control count (e.g., CEP17) of zero because these tiles generally are ignored, and this can introduce a bias. Another issue is determining the optimum bucket size to use in determining histograms.

9. Other Analysis Methods

Estimating "Tumor Proportion" and "Tumor Ratio" by Simultaneous Equations

In various further embodiments, other techniques are used to estimate one or more of $R_O$, R and P. From the discussion above, it follows that: $R_O=(1-P)+PR$. Thus, finding the tumor ratio of a mixed set of cells given the overall ratio $R_O$ becomes a matter of estimating the tumor proportion P. By analogy, the same is expected to be at least approximately true for a set of tiles placed over a mixed set of cells.

According to further embodiments, a further method estimates P and R. The method is first described for mixed populations of complete (not truncated) amplified and unamplified cells, however, as will be described below, this method can also be directly applied to tiles analysis. For unamplified cells, $\Sigma t_i=\Sigma c_i$ across all unamplified cells i. For amplified cells, $\Sigma t_j=\Sigma Rc_j=R\Sigma c_j$ across all amplified cells j. Again using the notion of "tumor proportion" based on the total CEP17 counts in the amplified and the unamplified cells:

$$\Sigma t_k = (PR+(1-P))\Sigma c_k \quad \text{(Eqn. 4),}$$

where the sums are taken across all cells k, both tumor and normal.

Equation 4 has two unknowns; generally to solve it completely there is needed a different equation relating the spot counts and P and R. According to specific embodiments, the invention does this by considering the squares of the per-cell (or per-tile) spot counts, as described below.

For the unamplified cells, $\Sigma(t_i)^2=\Sigma(c_i)^2$, where the summation is across all the unamplified cells i. For the amplified cells, $\Sigma t_j^2=\Sigma(Rc_j)^2=R^2\Sigma c_j^2$, where the summation is across all the amplified cells j. Over all cells (or tiles) k, $$\Sigma t_k^2 = (PR^2+(1-P))\Sigma c_k^2 \quad \text{(Eqn. 5).}$$

Equations 4 and 5 form a pair of simultaneous equations for P and R. The solutions are as follows. From equation 4, $P=(\Sigma t_k - \Sigma c_k)/((R-1)\Sigma c_k)$. From equation 5, $P=(\Sigma t_k^2)/((R^2-1)\Sigma c_k^2)$. Remembering that $(R^2-1)=(R-1)(R+1)$, it follows that $$R = \Sigma c_k(\Sigma t_k^2 - \Sigma c_k^2)/(\Sigma c_k^2(\Sigma t_k-c_k))-1 \quad \text{(Eqn. 6).}$$

Rewriting equation 4, $$P=((\Sigma t_k/\Sigma c_k)-1)/(R-1) \quad \text{(Eqn. 7).}$$

Application to Tiles

The method as described above for whole cells is, according to specific embodiments of the present invention, applied exactly to tiles-based analysis as if each tile were to contain either complete amplified cells only or complete unamplified cells only. To the extent that this situation does not apply because (i) the tiles may contain a mixture of cell types, (ii) the cells may be truncated by the tiling, the model is approximate. Experience with a training set of 73 samples has nevertheless shown that this model does work well in many of those cases where there are two cell populations in the data sampled by the tiles.

Thus, the method described can also be applied to tiles data. However, an issue to be considered is: will the solution to P always lie in the expected range (0<P<1), and similarly will R always be positive? The answer is "no." For example, if the two populations both have ratios different from 1.0, then the entire model is generally inappropriate, and neither P nor R will likely be sensible. This case generally cannot be distinguished a priori. A further issue is that the method above implicitly assumes that tiles containing amplified cells have the same distribution of CEP17 spot counts as tiles containing normal cells; if this assumption is incorrect then the method is approximate and this may explain some observed cases where P is computed to lie outside the range [0, 1].

Experience with an experimental data set has shown that when using the above method, the following can effectively deal with cases where the distributions lead to unlikely values of P and/or R. If the estimate of P is >1.0, then likely the sample is almost all tumor. In this case, it is appropriate to report $R=R_O$. If the estimate of P is <0.1, then P=0.1 is substituted and the corresponding value of R computed from equation 7. If R is computed to be negative, then again report $R=R_O$.

In further embodiments of the invention, to resolve this sort of case, a more complex model including a weighted sum of the per-tile spot counts cubed can be introduced, leading to three simultaneous equations in two different ratios and one proportion.

Estimating "Tumor Proportion" and "Tumor Ratio" by Expectation Maximization

According to further embodiments, an Expectation Maximization (EM) method can be used to estimate P and R. EM algorithms are well-known in the art for estimating a mixture of statistical probability distributions from a data set hypothesized to be drawn from such a mixture. According to specific embodiments of the present invention, the set of data comprises the set of pairs $(t_i, c_i)$ test spot count $(t_i)$ and control spot count $(c_i)$ on a per tile (or per cell or per other sampling region used) basis. The hypothesis used is that these are generated by a mixture or combination of two underlying bivariate probability distributions: one that jointly generates test and control spot counts for tiles (or sampling regions) containing unamplified cells, and the other that jointly generates test and control spot counts of tiles (or sampling regions) containing amplified tumor cells.

In these embodiments, the EM algorithm is given initial starting values (defined in more detail below) of two parameter sets respectively describing bivariate probability distributions of spot count pairs in unamplified tiles and in amplified tiles. By comparing each tile's spot count pair with each of the two bivariate probability distributions, the relative likelihood that the tile was generated by the first probability distribution and the relative likelihood that the tile was generated by the second probability distribution are computed.

The pairs of relative likelihoods for every tile are then used as weighting factors in a re-estimation of the parameters of the two generating bivariate probability distributions and can also be used to estimate the relative proportions of each component distribution in the mixture. This entire process is iterated until the bivariate probability distribution parameters have converged to stable values.

Thus, according to specific embodiments of the present, an iterative EM process is used to assign to each tile (or other sampling region) the probabilities that it contains amplified or unamplified material respectively. The set of these probabilities for all tiles results in an estimate of the amplified tumor ratio and the proportion of amplified material. Further details of EM methods in general are described in [J. A. Bilmes, A gentle tutorial of the EM Algorithm and its application to parameter estimation for Gaussian mixture and hidden Markov models, ICSI-TR-97-021, International Computer Science Institute, Berkeley, Calif. 94704, April 1998, www.cs.ucr.edu/~stelo/cs260/bilmes98gentle.pdf].

Following convergence of the EM algorithm, the ratio R implied by each of the two bivariate probability distributions can be computed by dividing each test count mean distribution by the corresponding control count mean. The higher ratio is reported as the Tumor Ratio (R). The relative proportion of the corresponding distribution is reported as the Proportion of amplified material (P).

According to further embodiments of the present invention, each bivariate probability distribution used in the EM algorithm is the product of a univariate Poisson distribution for the test spot count and a univariate Poisson distribution for the control spot count.

According to further embodiments of the present invention, a spot count of zero in a tile may be caused either by a statistical sampling effect or by failure of hybridization in this portion of the sample, and these two causes are indistinguishable from the data. It is therefore beneficial not to use the spot counts of any tile with either a test spot count of zero or a control spot count of zero. It is then beneficial that estimation of each univariate Poisson distribution is modified to take account of the deliberate exclusion from the set of observed tiles of any tile with either a test spot count of zero or a control spot count of zero. This can be done in further embodiments by using a Monte Carlo method to generate correction factors between an underlying Poisson mean and the corresponding observed mean when tiles with zero spot count are excluded.

According to further embodiments of the present invention, the starting values for the mean spot counts for both of the control distributions (e.g., CEP17) are set to the mean spot count in all tiles. The mean spot counts of the test distributions (e.g., Her2) are set so that the ratio of the test mean to the control mean is 1.0 in the first distribution (representing the unamplified material) and $1+2*(R_O-1)$ in the second distribution (representing the amplified material). This models the starting assumption that approximately 50% of the material is amplified.

According to further embodiments of the present invention, a convergence criterion may be used to terminate iteration of the EM algorithm. This criterion is that at least 20 iterations have passed, and that the ratio of the mean test count to the mean control count of neither distribution has changed by more than 0.001 from the preceding iteration.

According to further embodiments of the present invention, the spot count pair data can also be fitted with a single bivariate distribution by well-known statistical techniques. The goodness of fit of the single bivariate distribution may be compared with the goodness of fit of the mixture of two bivariate distributions by computing the joint likelihood of the set of spot count pairs of all tiles if generated by the single bivariate distribution, and the joint likelihood of the set of spot count pairs of all tiles if generated by the mixture of two bivariate distributions. If the single bivariate distribution has higher joint likelihood, then the overall ratio $R_O$ is reported. If the mixture distribution has higher joint likelihood, then the higher ratio from the mixture as defined above is reported.

According to further embodiments of the present invention, it is a common observation that in a population of samples, better performance is obtained by methods that have fewer free parameters requiring estimation. It is then beneficial to constrain the EM algorithm distribution fitting process by requiring that the ratio of one bivariate distribution is identically 1.0 after every iteration.

Further Example

In a further embodiment, a mixture of two distributions is used, one representing amplified and the other unamplified tiles, the distributions being indexed by k. The Her2 and CEP17 spot counts are each modeled by a Poisson distribution. The initial Poisson means $\mu_{hk}$ (Her2 counts) and $\mu_{ck}$ (CEP17 counts) are derived by a preliminary analysis of the data. The initial relative weight given to each component distribution in the mixture is $a_k=0.5$.

The spot count pair $(h_i, c_i)$ from tile i (i=1 ... N) is then compared with each distribution in the mixture, and the relative likelihood of the pair being explained by each distribution is calculated. Let $w_{i,k}=\alpha_k*P(h_i;\mu_{hk})*P(c_i;\mu_{ck})/\Sigma_{j=1,2}\alpha_j*P(h_i;\mu_{hk})*P(c_i;\mu_{ck})$ be the per-lite relative likelehoods for tile i and component distribution k. Here, $P(n;\mu)$ means the probability of n given a Poisson distribution with mean $\mu$. (Note that it has been assumed that the Her2 and CEP17 spot counts are independent; it has been found experimentally that this simplifying assumption leads to more accurate results than a model in which covariance must also be estimated.)

A revised model is then calculated by applying the per-tile relative likelihoods obtained in step 2 to re-compute the parameters of each distribution k=1,2 as follows:

$$\alpha_k = \Sigma_i w_{i,k}/N$$

$$\mu_{hk} = \Sigma_i w_{i,k} h_i / \Sigma_i w_{i,k}$$

$$\mu_{ck} = \Sigma_i w_{i,k} c_i / \Sigma_i w_{i,k}$$

The two stages: (1) compute per-tile relative likelihoods to each distribution and (2) update the per-distribution weights and mean values, are iterated until a convergence criterion is satisfied.

Example of the Behavior of the EM Method on a Set of Test Samples

Experimental results have shown that EM methods according to specific embodiments of the invention can provide better automated results. In these experiments, regions were deliberately chosen so as to contain both amplified and unamplified cells.

In this description, the following abbreviations are used.

"RR" is ground truth ratio for a sample, the average ratio of amplified cells scored by two or sometimes three observers.

"$R_O$" is the overall ratio computed from the automatic spot counts in all tiles in the fields of view.

"EM" is the ratio computed by EM analysis on all tiles from all fields of view. "EM-C" means EM where the lower-ratio population is constrained to have ratio=1.0. "EM-U" means unconstrained EM.

"CV" is coefficient of variation (standard deviation/mean). We use it to measure the difference for each sample between ground truth ratio and a ratio computed by tiles analysis. The mean over a set of samples is a measure of the method's precision.

"SCV" is "signed CV". The mean over a set of samples is a measure of the method's bias.

"Biasat RR=2" is the predicted bias of the measurement method at the PathVysion amplified decision ratio of RR=2.

"FP", "FN" are the numbers of false positive (RR<2, R>2) and false negative (RR>2, R<2) samples.

In verification experiments, we evaluated ratio estimation methods by comparing their mean SCV, mean CV, and numbers of FPs and FNs on two standard data sets. The first data set was a combined Training and Alpha Test data set, comprising close to 300 tumor samples, which are believed to be representative of routine samples. Because it was generally unknown whether each of these samples had homogeneous spot counts throughout, or contained two cell populations with respectively normal and amplified Her2 spot counts, a further set of 20 samples was scanned in which the operator deliberately chose regions of invasive tumor material and also regions comprising a similar amount of normal tissue. Additionally, 16 samples for which there was unequivocal evidence that each contained two cell populations were selected from the Training and Alpha Test sets. Thus every one of these 36 samples were known to contain two different cell populations in approximately equal proportions. Results were as follows:

Training Plus Alpha Test Samples

| Method | SCV | CV | FP | FN | Bias at RR = 2 |
| --- | --- | --- | --- | --- | --- |
| RO | −0.019 | 0.118 | 1 | 6 | 0.021 |
| EM-C | 0.006 | 0.116 | 2 | 6 | 0.057 |
| EM-U | 0.037 | 0.123 | 2 | 6 | 0.092 |

36 Mixed-Distribution Samples

| Method | SCV | CV | FP | FN |
| --- | --- | --- | --- | --- |
| RO | −0.291 | 0.300 | 0 | 2 |
| EM-C | −0.166 | 0.218 | 0 | 2 |
| EM-U | −0.052 | 0.188 | 0 | 2 |

Bias at RR=2.0 was not computed for the 36-sample set because this set had samples with predominantly high tumor ratios. From the SCV and FN values, it can be seen that overall ratio RO tends to underestimate tumor ratio (because the normal ratio material is not excluded by this method). EM corrects this underestimation substantially. EM-U appears to make a better correction than EM-C in the selected two-population samples, but leads on average to a slight overestimation of ratio in the larger and more representative Training plus Alpha Test set.

10. Other Considerations and Optional Modes of Operation

Inclusion of Sufficient Tumor Cells

There is a risk that tiling the FOVs surrounding a marked point may select too little tumor material and/or too few tumor cells. One solution is based on enhanced interactive review capabilities, and proceeds as follows. (1) Let the system capture FOVs centered around the marked point. (2) Present a mosaic image of the FOVs at sufficiently low resolution that all FOVs centered around the marked point are simultaneously visible on the screen to an operator. This will allow the user to see the tissue architecture surrounding the marked point. (3) If the operator indicates by clicking the appropriate button on the screen that the entire mosaic is comprised of invasive tumor cells, continue with the tiles method as described above. (4) If the architecture shows some tumor and some non-tumor regions, have the operator indicate the tumor boundary using an appropriate input device (such as a mouse or light pen) on the computer system. (5) Use the user indicated boundary to select the tiles that lie within the tumor region from the full tiling. (6) Use selected tiles to populate the histogram and the gallery. (7) Repeat for every marked point.

It will be understood according to specific embodiments that this method achieves the following: (1) A visual review of the marked point, to verify that it marked a tumor region (In many samples, regions of invasive tumor can be recognized by DAPI staining, and if this determination cannot be made with confidence from the DAPI image alone, then sufficient of the tissue architecture is presented in the DAPI image to allow for a comparison with an H&E slide on an adjacent light microscope); (2) Guarantee that the selected set of tiles contains tumor cells, at maximal concentration with respect to normal cells.

Optimal Size of Tiles

According to further embodiments of the invention, larger tiles can be used and be expected to have better behaved ratios because the CEP17 denominator is larger, but there is a higher risk of mixing tumor and normal cells.

Other Presentation

According to further embodiments of the invention, data can be expressed as a three dimension plot, standard X and Y for the surface of a slide, and Z representing the Her-2/CEP17 ratio in each of the tiles.

Cells-Based Options

In further embodiments, it is possible to perform counts in individual cells, plot the ratios in histogram form, and if the histogram has two peaks (representing normal cells and amplified cells), report the ratio of the upper peak. In effect, this automatically eliminates normal cells from the overall ratio and according to specific embodiments of the invention is adapted as a useful technique in automated analysis, with adjustments for the issue of artifact ratios in truncated cells. However, this method is different from that described above in that (i) it is based on cells and thus is less suitable for automation, (ii) it extracts the ratio from the histogram by a different technique, (iii) it generally only works for cases where the tumor is highly amplified (e.g., it would likely not work if R=1.5 and probably not if R=2.0.)

This technique, used alone, may be similar to earlier work. According to specific embodiments of the invention, however, this or a similar technique can be provided as an option in a system that also can perform tiles-based analysis and this technique can be performed and reported along with tiles-based analysis in some embodiments for comparison. Thus, in further embodiments, counting in tiles can be used in addition to one or more methods based on counting spots in well-separated nuclei.

In further embodiments, it is possible to perform counts in individual cells, and apply the method for ratio estimation by simultaneous equations. This procedure may be used to identify the spot counts of two distinct populations of cells in samples in which identification of whole cells is relatively straightforward, for example in samples prepared from liquid cell suspensions.

In further embodiments, it is possible to perform counts in individual cells, and apply the method for ratio estimation by expectation maximization. This procedure may be used to identify the spot counts of two distinct populations of cells in samples in which identification of whole cells is relatively straightforward, for example in samples prepared from liquid cell suspensions.

Highly Amplified Cells

Dilution by normal cells on the tile method can also be overcome by a consideration that if there are two or three highly amplified tumor cells (Her2 to CEP17 ratios in range of >5, for example) out of a field of several hundred cells in a tumor region, that is sufficient to make the diagnosis of amplification. However, in the case of such rare amplified cells, machine scoring according to specific embodiments of the present invention is expected in some cases to prove highly advantageous. In (possibly uncommon) cases where a single tumor mass has a heterogeneous population of tumor cells containing mostly unamplified tumor cells and just a few amplified tumor cells, machine scoring is expected in some cases to increase the "yield" of amplified samples by finding evidence (e.g. via tiles analysis) of the rare amplified cells. Note that such "rare-amplified-cell" tumors would probably also be "rare-overexpressing-cell" tumors, and so may likely be overlooked by immuno-histochemistry (IHC) techniques. Further, in the case where such rare cells are buried in a dense mass of tumor material, a visual scorer likely will not score such cells because they are not well separated. Such cells will also generally be very difficult or impossible for a cell-based computer algorithm to find. However, a tiles method can be used to analyze tumor masses where the cell nuclei cannot be separated. According to specific embodiments of the present invention, a gallery display will show the highest ratio (and/or, for example, the highest Her2 count) tiles first, then even very rare amplified cells will generally be shown to the user.

User FOV Selection With Histogram Analysis

In further embodiments, histogram analysis can simplify the process of initial tumor identification. Generally, a pathologist or technician scans visually using a triple-pass filter to identify invasive regions for counting. When such a region is found, center it in the visual field and press a key. This will record a point on the slide for counting. Later in the automated counting phase, such marked points will be used as the centers of expanded regions of pre-defined size, and all cells in such region will be counted. The histogram analysis will then discriminate normal from amplified cells. This procedure eliminates the need to draw a region boundary on a screen image, which is regarded as a disadvantage of earlier proposed procedures.

User Review of Tiles Analysis

While in some embodiments, tiles placement and analysis is performed with little user intervention or review, in a further embodiment, an example user scenario can allow a skilled user to interact with the analysis process and confirm or modify certain automated placement and/or analysis findings. An example of such a process is as follows:

1. Each FOV is presented to a user with the tile boundaries superimposed (perhaps as dashed or gray lines, i.e. generally not too intrusive). The user is asked to approve or not approve the FOV and the choice of tiles, perhaps following an instruction such as "approve this FOV if and only if the set of tiles contains at least 10% tumor cell material".

2. If fewer than X (such as, for example, four) FOVs are accepted by the above criterion, the sample generally will automatically fail quality control (QC). This may imply sample failure for those cases where the tumor is very tiny or the tumor cells are very dispersed, which may be desirable is some situations.

3. The gallery displays tiles from approved FOVs only, sorted by spot count, or by ratio. Optionally, the user can, if necessary, reject tiles or correct spot counts, as in cells gallery systems.

4. The tiles ratio histogram is displayed. An automatic analysis suggests an overall ratio for the tumor cell population, with the user given some ability to confirm or modify the final reported ratio (as always, with suitable tracking).

Simulation Studies

Some parts of the tiles method, and particularly analysis of the histogram of per-tile ratios, have been investigated by simulation studies in order to evaluate the likely performance of tile-based ratio estimation across the range of tumors likely to be encountered in practice, by modeling the following aspects as random distributions: (1) Tiles will sample differing amounts of nuclear material, from varying numbers of cells; (2) The proportion of tumor to normal cells in the tumor will vary among tumors: and (3) Truncation of cells by the edges of the tile and by the sectioning of the tumor, leading to loss of FISH signals from each nucleus.

Effect of Tile Size

Further simulation investigations of a targeted tiles approach to, for example, Her2 scoring are discussed below. Simulation studies have found that the removal of the predicted background of normal ratio tiles works well. In this simulation, first a very large set of tiles was generated assuming an unamplified tumor. The resulting unamplified tumor histogram was then scaled to the observed histogram in the region with ratios <=1.5. The scaled unamplified tumor histogram was then subtracted from the observed histogram (with negative values set to zero). Remaining positive counts for ratios <1.5 were also set to zero. Note that the same unamplified tumor histogram was used for the experiments reported here. Data reported here have employed that operation. An advantage of using larger tiles is that fewer will be rejected on account of the CEP17 count (i.e., the ratio denominator) being too small. A disadvantage is that larger tiles are more likely to consist of a mixture of tumor and normal cells, and less likely to consist of either just tumor or just normal cells. In particular examples, it has been found that the smaller the tile size, the better the estimate (from the histogram peak) of the true ratio. On the other hand, 27% of all size=1 tiles were rejected by the CEP17 minimum count criterion, as against 5% at size=2 and 0% at size=4.

11. Embodiment in a Programmed Information Appliance

Figure 6:
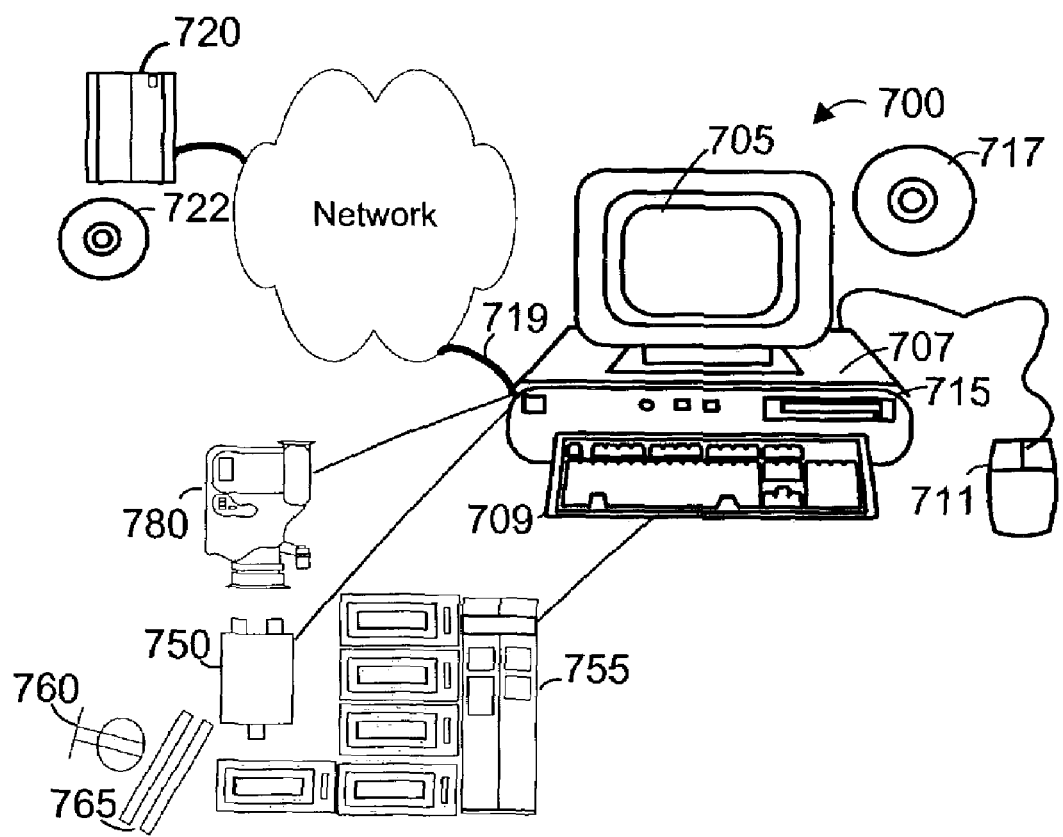
FIG. 6 is a block diagram showing a representative example logic device in which various aspects of the present invention may be embodied.

FIG. 6 is a block diagram showing a representative example logic device in which various aspects of the present invention may be embodied. As will be understood from the teachings provided herein, the invention can be implemented in hardware and/or software. In some embodiments, different aspects of the invention can be implemented in either client-side logic or server-side logic. Moreover, the invention or components thereof may be embodied in a fixed media program component containing logic instructions and/or data that when loaded into an appropriately configured computing device cause that device to perform according to the invention. A fixed media containing logic instructions may be delivered to a viewer on a fixed media for physically loading into a viewer's computer or a fixed media containing logic instructions may reside on a remote server that a viewer accesses through a communication medium in order to download a program component.

FIG. 6 shows an information appliance or digital device 700 that may be understood as a logical apparatus that can perform logical operations regarding image display and/or analysis as described herein. Such a device can be embodied as a general purpose computer system or workstation running logical instructions to perform according to specific embodiments of the present invention. Such a device can also be custom and/or specialized laboratory or scientific hardware that integrates logic processing into a machine for performing various sample handling operations. In general, the logic processing components of a device according to specific embodiments of the present invention is able to read instructions from media 717 and/or network port 719, which can optionally be connected to server 720 having fixed media 722. Apparatus 700 can thereafter use those instructions to direct actions or perform analysis as understood in the art and described herein. One type of logical apparatus that may embody the invention is a computer system as illustrated in 700, containing CPU 707, optional input devices 709 and 711, storage media (such as disk drives) 715 and optional monitor 705. Fixed media 717, or fixed media 722 over port 719, may be used to program such a system and may represent a disk-type optical or magnetic media, magnetic tape, solid state dynamic or static memory, etc. The invention may also be embodied in whole or in part as software recorded on this fixed media. Communication port 719 may also be used to initially receive instructions that are used to program such a system and may represent any type of communication connection.

FIG. 6 shows additional components that can be part of a diagnostic system in some embodiments. These components include a microscope 750, automated slide stage 755, UV light source 760 and filters 765, and a CCD camera or capture device 780 for capturing digital images for analysis as described herein. It will be understood to those of skill in the art that these additional components can be components of a single system that includes logic analysis and/or control. These devices also may be essentially stand-alone devices that are in digital communication with an information appliance such as 700 via a network, bus, wireless communication, etc., as will be understood in the art. It will be understood that components of such a system can have any convenient physical configuration and/or appear and can all be combined into a single integrated system. Thus, the individual components shown in FIG. 6 represent just one example system.

FIG. 5 illustrates example user interfaces for grid tiling options according to the present invention.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

12. Other Embodiments

The invention has now been described with reference to specific embodiments. Other embodiments will be apparent to those of skill in the art. In particular, a viewer digital information appliance has generally been illustrated as a personal computer. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed:

1. A method of analyzing biological samples for determinable properties using a computer system comprising:
   capturing an image of said sample into a computer system;
   using said computer system, placing subarea outlines over said image according to a placement process, said subarea outlines being of a predefined shape, said predefined shape not determined by identifying edges or objects in said image;
   using said computer system, analyzing said image by scoring detectable characteristics of said image within one or more of said subarea outlines; and
   using said computer system, preparing an output from scored detectable characteristics of said image;
   outputting said output to a user to an information processing system;
   further wherein said placement process comprises an iterative search of said image comprising:
   searching said image to find a region of said image providing a desired signal strength of a detectable signal;
   placing a subarea outline over said region, thereby defining a subarea and a remaining area; and
   on said remaining area, iteratively continuing said searching and said placing until a stop condition is reached.

2. The method according to claim 1 wherein said sample comprises one or more of:
   a thin section from a tissue biopsy;
   a dense cellular monolayer prepared from disaggregated cells; or
   a smear preparation.

3. The method according to claim 1 wherein said image is produced using an extended focus process.

4. The method according to claim 1 wherein said image is a two-dimensional image.

5. The method according to claim 1 wherein said subareas comprise tiles and further wherein said placement process comprises one or more of:
   placing tile outlines such that outlines are abutting;
   placing tile outlines in a regular grid over said image,
   placing tile outlines such that outlines are not necessarily abutting; or
   placing tile outlines such that tile outlines do not necessarily cover said image.

6. The method according to claim 1 wherein said detectable signal is the total fluorescence intensity of a cellular nuclear stain.

7. The method according to claim 1 wherein said searching comprises searching for a subarea outline region that produces a highest value of said detectable signal.

8. The method according to claim 1 wherein said stop condition comprises determining that a placed subarea has a signal value with a predefined relationship to another value.

9. The method according to claim 8 wherein said another value is derived from one or more values found for one or more previously placed subareas.

10. The method according to claim 1 wherein said output further comprises:
an estimation of gene copy number.

11. The method according to claim 1 wherein said output further comprises:
detection of gene amplification.

12. The methods according to claim 7 wherein said signal value is measured using fluorescence in situ hybridization probes and/or DAPI.

13. The method according to claim 1 wherein said subarea outlines are one or more of:
roughly rectangular in shape;
roughly polygonal in shape; or
roughly circular in shape.

14. The method according to claim 1 wherein said subarea outlines are selected to have an area roughly equal to or slightly larger than a largest cross-sectional area of a largest expected cell in said sample.

15. The method according to claim 14 wherein:
said largest expected cell is a tumor cell.

16. The method according to claim 1 wherein said analyzing further comprises:
detecting two or more signal values in a determined subarea outline; and
calculating a value using a ratio of said two or more signal values.

17. The method according to claim 1 wherein said preparing further comprises:
in each subarea, computing a ratio from detectable signals;
computing an original histogram of said ratios;
computing a normal-corrected histogram of said ratios; and
from said normal-corrected histogram, estimating a ratio value for one or more cells in said sample.

18. The method according to claim 17 wherein said ratio comprises one or more of:
a first count divided by a second count;
a first signal value divided by a second signal value; or
a test value divided by a control value.

19. The method according to claim 17 wherein said analyzing further comprises:
determining one or more numerical results of said sample.

20. The method according to claim 17 wherein said analyzing further comprises:
in each subarea, computing a subarea ratio from said detectable signals;
computing a sample histogram of said subarea ratios;
determining a normalized reference histogram for said subarea ratios;
subtracting said normalized reference histogram from said sample histogram to produce a corrected histogram of said subarea ratios; and
estimating a ratio value of said sample from said corrected histogram.

21. The method according to claim 20 wherein said computing comprises converting per-subarea data to a sample histogram by allocating subarea data to generally equal-width buckets.

22. The method according to claim 21 wherein said estimating comprises detecting a notable shoulder or a second peak to the offset from a normal peak of said sample histogram.

23. The method according to claim 20 wherein said determining comprises:
fitting a normalized reference histogram to a normal peak in a mixed tumor sample histogram, and wherein said fitting comprises:
proportionately adjusting counts of reference histogram buckets so that a normalized reference histogram matches said sample histogram in an unamplified region as closely as possible.

24. The method according to claim 21 wherein said corrected histogram comprises
a third histogram where a count of every bucket is a difference between corresponding counts of said sample histogram and said reference histogram and wherein if said difference for any bucket is negative, that bucket's value is set to zero.

25. The method according to claim 20 further comprising:
estimating an amplified ratio R directly from said corrected histogram by a method comprising:
for each histogram bucket i, letting $p_i$ be the proportion of the count remaining after subtracting said normalized reference;
estimating the ratio R by $R = \Sigma(p_i c_i R_i)/\Sigma(p_i c_i)$;
where i indexes subareas;
t indicates test values;
c indicates control values; and
$R_i$ indicates a ratio $t_i/c_i$ of values of a single cell (or subarea), with $R_i$ set to 1 if $c_i=0$;
and further comprising:
verifying an estimated tumor ratio by calculating an amplified tumor proportion; and
not reporting the ratio R as verified unless said amplified tumor proportion exceeds a minimum threshold
further wherein said amplified tumor proportion P is estimated as $P=\Sigma(p_i c_i)/\Sigma c_i$.

26. The method according to claim 20 wherein a best shape of a normalized reference histogram is varied from sample to sample.

27. The method according to claim 17 wherein said plurality of subareas comprise a plurality of areas containing separated cells.

28. The method according to claim 17 wherein said plurality of subareas comprise a plurality of outlines placed in a regular grid.

29. The method according to claim 17 wherein said plurality of subareas comprise a plurality of targeted outlines placed by a placement method.

30. The method according to claim 1 wherein said analyzing further comprises:
estimating a tumor proportion and a tumor ratio by simultaneous equations.

31. The method according to claim 30 wherein said simultaneous equations comprise:

$\Sigma t_i = \Sigma c_i$ across unamplified subareas i;

$\Sigma t_j = \Sigma R c_j = R \Sigma c_j$, across amplified subareas j;

$\Sigma t_k = (PR+(1-P))\Sigma c_k$ across all subareas k;

wherein two unknowns P and R are related by considering squares of per-subarea spot counts.

32. The method according to claim 31 wherein said squares of per- subarea spot counts comprise:

$\Sigma(t_i)^2 = \Sigma(c_i)^2$, across unamplified subareas $i$;

$\Sigma t_j^2 = \Sigma(Rc_j)^2 = R^2 \Sigma c_j^2$, across amplified subareas $j$; and $\Sigma t_k^2 = (PR^2 + (1-P))\Sigma c_k^2$, over all subareas $k$.

33. The method according to claim 32 wherein P and R are determined form the formulas:

$P = (\Sigma t_k - \Sigma c_k)/((R-1)\Sigma c_k)$;

$P = (\Sigma t_k^2 - \Sigma c_k^2)/((R^2-1)\Sigma c_k^2)$, and it follows that $R = \Sigma c_k(\Sigma t_k^2 - \Sigma c_k^2)/(\Sigma c_k^2(\Sigma t_k - \Sigma c_k)) - 1$ and $P = ((\Sigma t_k/\Sigma c_k) - 1)/(R-1)$.

34. The method according to claim 33 wherein if an estimate of P is >1.0, R =$R_0$ is output.

35. The method according to claim 33 wherein if an estimate of P is <0.1, then P=0.1 is used to compute R; and if R is computed to be negative, R =$R_0$ is output.

36. The method according to claim 1 wherein said analyzing further comprises:
using an expectation maximization method to estimate an output from said scored detectable characteristics.

37. The method according to claim 1 wherein said analyzing further comprises:
using an expectation maximization method to estimate a tumor proportion and a tumor ratio of said sample.

38. The method according to claim 1 wherein said preparing further comprises:
in each subarea, determining a data set of one or more detectable characteristics; and
using an expectation maximization method to estimate an output from said scored detectable characteristics.

39. The method according to claim 36 wherein said analyzing further comprises:
using a set of per subarea scored detectable characteristic data pairs $(t_i, c_i)$ representing test and control detectable values in an expectation maximization method.

40. The method according to claim 1 wherein said analyzing further comprises:
providing plausible initial starting values to said expectation maximization method, said starting values describing a first bivariate probability distribution of data sets in unamplified subareas and describing a second bivariate probability distribution of data sets in amplified subareas;
comparing a an unamplified subarea's data set with each of said bivariate probability distributions to determine a relative likelihood that said subarea data set was generated by said first bivariate probability distribution and a relative likelihood that said subarea data set was generated by said second bivariate probability distribution;
using said pairs of relative likelihoods for a plurality of subareas as weighting factors in a re-estimation of the parameters of the two generating bivariate probability distributions;
using said pairs of relative likelihoods for a plurality of subareas to estimate the relative proportions of each component distribution;
iterating the process until the bivariate probability distribution parameters have converged to stable values;
after convergence of expectation maximization method, computing a ratio implied by each of the two bivariate probability distributions by dividing each test count mean distribution by the corresponding control count mean;
reporting a higher ratio as a Tumor Ratio; and
reporting a relative proportion of a corresponding distribution as a Tumor Proportion.

41. The method according to claim 40 further wherein:
each bivariate probability distribution used in the expectation maximization method is a product of a univariate Poisson distribution for test values and a univariate Poisson distribution for control values.

42. The method according to claim 40 further wherein:
spot counts of any subarea with either a test value of zero or a control value of zero are not used.

43. The method according to claim 42 further wherein:
estimation of each univariate Poisson distribution is modified to take account of deliberate exclusion from the set of observed data of any subarea with either a test count value of zero or a control count value of zero; and
each univariate Poisson distribution is modified using a Monte Carlo method to generate correction factors between an underlying Poisson mean and the corresponding observed mean when subareas with zero values are excluded.

44. The method according to claim 40 wherein said analyzing further comprises:
fitting data with a single bivariate distribution using known statistical techniques.

45. The method according to claim 40 further comprising:
comparing a goodness of fit of the single bivariate distribution with the goodness of fit of the mixture of two bivariate distributions by computing the joint likelihood of the data set of all subareas if generated by the single bivariate distribution, and the joint likelihood of the data set of all subareas if generated by the mixture of two bivariate distributions; and
if the single bivariate distribution has higher joint likelihood, then reporting the overall ratio $R_0$ instead of the higher ratio.

46. The method according to claim 40 further comprising:
constraining the fitting process by requiring a ratio of one bivariate distribution to be identically 1.0 after every iteration.

47. The method according to claim 40 wherein said plurality of subareas comprise a plurality of areas containing separated cells.

48. The method according to claim 40 wherein said plurality of subareas comprise a plurality of outlines placed in a regular grid.

49. The method according to claim 40 wherein said plurality of subareas comprise a plurality of targeted outlines placed by a placement method.

50. The method according to claim 40 wherein said plurality of subareas comprise a plurality of areas containing separated cells.

51. The method according to claim 40 wherein said plurality of subareas comprise a plurality of outlines placed in a regular grid.

52. The method according to claim 44 wherein said plurality of subareas comprise a plurality of targeted outlines placed by a placement method.

* * * * *